United States Patent
Grams et al.

(10) Patent No.: US 9,512,896 B2
(45) Date of Patent: Dec. 6, 2016

(54) REDUCING VIBRATION OF A CANTILEVERED PATIENT SUPPORT SURFACE

(71) Applicant: General Electric Company, Schenectady, NY (US)

(72) Inventors: Robert Scott Grams, Waukesha, WI (US); Philip Olikara, Waukesha, WI (US); Adam Clark Nathan, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/584,363

(22) Filed: Dec. 29, 2014

(65) Prior Publication Data

US 2016/0186832 A1   Jun. 30, 2016

(51) Int. Cl.
*F16M 13/00* (2006.01)
*F16F 15/02* (2006.01)
*A61B 6/04* (2006.01)
*F16M 11/22* (2006.01)

(52) U.S. Cl.
CPC .......... *F16F 15/022* (2013.01); *A61B 6/0428* (2013.01); *F16M 11/22* (2013.01)

(58) Field of Classification Search
CPC .. F16M 11/10; F16M 11/38; F16M 2200/044; F16M 11/22; F16F 15/022; A61B 6/0428
See application file for complete search history.

(56) References Cited

U.S. PATENT DOCUMENTS

| | | | |
|---|---|---|---|
| 5,107,121 A | 4/1992 | Lim et al. | |
| 6,058,158 A | 5/2000 | Eiler | |
| 6,205,743 B1 | 3/2001 | Castellari | |
| 6,217,496 B1 | 4/2001 | Lindem | |
| 2007/0047186 A1* | 3/2007 | Jang | F16M 11/04 361/679.06 |
| 2012/0248048 A1* | 10/2012 | Wu | F16M 11/10 211/26 |

* cited by examiner

*Primary Examiner* — Amy Sterling
(74) *Attorney, Agent, or Firm* — Dean D. Small; The Small Patent Law Group, LLC.

(57) ABSTRACT

A system and method for reducing vibration of a cantilevered patient support surface are provided herein. A system includes a spring and roller coupled with the spring. The spring creates an upwards spring bias on the patient support surface. The roller is coupled with the spring via a roller lever arm. A frictional resistance at the roller arm and an upward directed spring bias enables the roller to maintain constant contact with the patient support surface.

9 Claims, 5 Drawing Sheets

100

200

400

REDUCING VIBRATION OF A CANTILEVERED PATIENT SUPPORT SURFACE

BACKGROUND OF THE INVENTION

Various technologies exist wherein portions of a patient are imaged to study tissues or organs within the body. For example, nuclear medicine includes techniques where a radiopharmaceutical is introduced to a patient that causes the emission of photons from the body of the patient. The radiopharmaceutical may concentrate in particular tissues of the body, indicating tissue metabolic activity at the site of concentration and emitting a higher amount of photons from the site of concentration. Images may be reconstructed from photons observed during Positron Emission Tomography (PET) scan. PET scans may be combined with computerized tomography (CT) scans to develop an image of tissues and organs of a patient.

A patient is supported by a patient support surface and then moved within a gantry on the patient support surface to obtain PET scans and CT scans of the patient's anatomy. The movement of the patient to obtain PET scans and CT scans can create small vibrations that can create artifacts within an image obtained from a PET or CT scan. Thus, removing the vibrations results in a higher quality image.

SUMMARY OF THE INVENTION

An embodiment relates to a system for reducing vibration of a cantilevered patient support surface. A system includes a spring and roller coupled with the spring. The spring creates an upwards spring bias on the patient support surface. The roller is coupled with the spring via a roller lever arm. A frictional resistance at the roller arm and an upward directed spring bias enables the roller to maintain constant contact with the patient support surface.

Another embodiment relates to method for reducing vibration of a cantilevered patient support surface. The method includes providing an upward spring bias and a frictional resistance and maintaining constant contact with the cantilevered patient support surface. The method also includes creating a constant deflection wherein the patient anatomy does not change in vertical position during image data acquisition.

Still another embodiment relates to a device for cradle support. The device includes a base frame, a friction disc, and a roller. The base frame is coupled with a plurality of torsion springs attached to an friction setting compression die spring. The plurality of torsion springs and the friction disc surround a roller lever arm, and the roller lever arm is coupled to the roller.

BRIEF DESCRIPTION OF THE DRAWINGS

The present techniques will become more fully understood from the following detailed description, taken in conjunction with the accompanying drawings, wherein like reference numerals refer to like parts, in which.

In some cases, the same numbers are used throughout the disclosure and the figures to reference like components and features. Numbers in the 100 series refer to features originally found in FIG. 1; numbers in the 200 series refer to features originally found in FIG. 2; and so on.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

As discussed above, a patient is supported by a patient support surface and then moved within the gantry on the patient support surface to obtain PET scans and/or CT scans of the patient's anatomy. As used herein, the patient support surface includes, but is not limited to, a cradle movably attached to a table support. In the embodiments discussed herein, a device is used to dampen vibrations that can distort images obtained during imaging. The device maintains constant contact with the patient support surface. Thus, a technical effect of at least one embodiment includes high quality imaging resulting from a mechanism for reducing vibrations on a cantilevered patient support surface. In particular, the mechanism may be a device with a roller that maintains constant contact with the patient support surface.

A cantilevered patient support surface offers several advantages for diagnostic imaging. For example, the patient weight on the support surface causes initial deflection of the cradle, and then stays at constant deflection, sometimes referred to as "constant sag." Once at a constant deflection, any part of the anatomy under study does not significantly change in a vertical position throughout the entire image data acquisition process. This offers improvements in diagnostic imaging performance and accuracy. Additionally, when the patient mass is located well beyond the cradle mounting provisions, the extended mass can create continuous vertical position change or vibrations. As described herein, vibrations are any vertical position change of the patient support surface. The sensitivity of modality units, such as CT scanners, can easily detect small changes in vertical displacement, creating undesirable scan image artifact errors. However, the device described herein enables a constant deflection well beyond the cradle mounting provisions, thereby eliminating undesirable scan image artifact errors.

Figure 1:
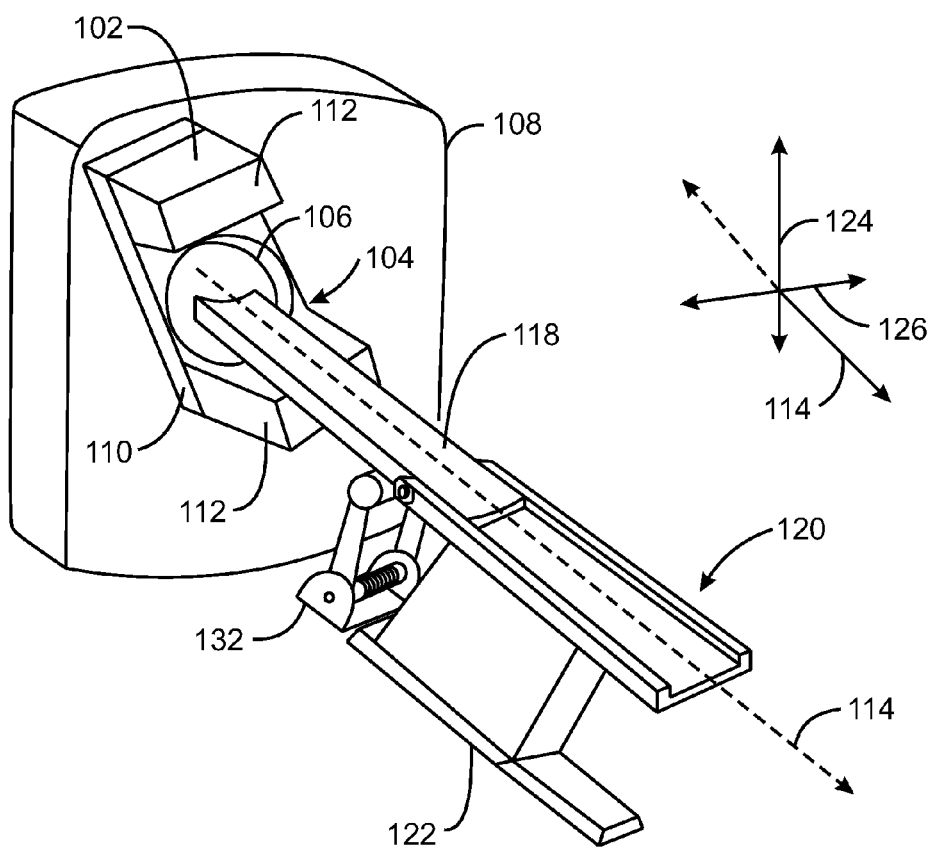
FIG. 1 is a perspective view of a medical imaging system including a cantilevered patient support surface and medical imaging gantry.

FIG. 1 is a perspective view of a medical imaging system 100 including a cantilevered patient support surface and medical imaging gantry. The imaging system 100 may be any type of imaging system, including a multi-modality imaging system. For example, the imaging system 100 may include one or more types of imaging modality units, such as a Positron Emission Tomography (PET) modality unit, a Single Photon Emission Computed Tomography (SPECT) modality unit, a Computed Tomography (CT) modality unit, an ultrasound modality unit, a Magnetic Resonance Imaging (MRI) modality unit, an X-Ray radiography or fluoroscopy modality unit, or any other modality unit capable of generating images of a region of interest of a patient. In embodiments, the imaging system 100 is a medical imaging system. The various embodiments described herein are not limited to medical imaging systems for imaging human subjects, and may include, for example, veterinary systems. As used herein, the term "patient" may refer to a human patient or any other animal.

Referring to FIG. 1, the imaging system 100 includes an imaging modality unit 102 that enables the imaging system 100 to scan a patient (not shown) in a first modality positioned at a field-of-view (FoV) 104. The imaging system 100 may also include a nuclear medicine imaging system that may be positioned around a bore 106. Nuclear medicine includes various techniques where a radiopharmaceutical is introduced to a patient to cause emission of photons from the body of the patient. The radiopharmaceutical may concentrate in particular tissues of the body, indicating tissue metabolic activity at the site of concentration and emitting a higher amount of photons from the site of concentration. The nuclear medicine cameras used to detect photons may be positioned about the bore 106. The nuclear medicine cameras may be, for example, gamma cameras, SPECT detectors, and/or PET detectors, configured to observe the photons that occur in a coincident event as emitted from a patient that has been introduced to a radiopharmaceutical. In an example, the nuclear medicine cameras may form an entire ring structure surrounding the bore 106. The ring structure may be a partial ring structure about the bore 106.

The FoV 104 may extend throughout a width of the bore 106, or the FoV 104 may be smaller than the bore 106. The bore 106 is at the center of a gantry 108. The gantry 108 includes a rotor 110 that supports one or more modality cameras 112. In an example, the imaging system 100 includes a stationary ring structure forming a first modality unit, and an imaging modality unit 102 combined with the rotor 110 and modality cameras 112 to form a second modality unit. Accordingly, the imaging system 100 may include multiple imaging modality units for various types of scans.

The rotor 110 may be configured to rotate the modality cameras 112 about a longitudinal or examination axis 114 that extends through the bore 106 of the imaging system 100. The bore 106 extends through the gantry 108 along the longitudinal axis 114. The bore 106 is sized and shaped to enable a patient (not shown) to be moved into and out of the bore 106. The patient may be moved in and out of the bore 106 on an imaging or patient cradle 118. As illustrated, the patient cradle 118 is extended through the bore 106. The patient cradle 118 is configured to support a patient in a desired or predetermined position within the FoV 104. The patient cradle 118 may extend from atop a table structure 120 to position a patient within the bore 106. The patient cradle 118 and table structure 120 are supported by a pedestal 122. In some embodiments, the pedestal 122 is configured to selectively move the patient cradle 118 from atop the table structure 120 along the longitudinal axis 114. Moreover, in some embodiments, the pedestal 122 is configured to selectively move the patient cradle 118 to desired elevations in a direction along a vertical axis 124. Furthermore, in some embodiments, the patient cradle 118 may also be configured to move laterally or side-to-side (e.g., left-to-right) along a lateral axis 126.

At the beginning of a medical image data acquisition process, the patient cradle 118 is disposed directly on top of the table structure 120. In other words, the patient cradle 118 is positioned outside of the FoV 104 and the bore 106. The patient is positioned on the patient cradle 118, and the pedestal 122 activates a mechanical structure that moves the patient into the bore 106 atop the patient cradle 118. The anatomy of the patient is imaged within the FoV 104. In some procedures, the patient is moved several times to obtain successive axial scan images, since the desired imaging region may not fit completely within the FoV 104.

When the patient table is moved during a medical image data acquisition process, small vibrations due to the movement of the patient cradle 118 may create stair step artifacts when successive axial scan images are stitched together. In embodiments, the vibrations may be created by the mechanical components of the pedestal 122 moving the patient cradle 118. As the size of the desired imaging region increases, the artifact error also increases. Error may also result from deflection of the patient cradle 118. The farther the patient cradle 118 is extended from the atop the table structure 120, the more deflection of the patient cradle 118 is present along the vertical axis 124. Deflection is higher for heavier patients as the patient cradle 118 is extended from the table structure 120.

A device 132 supports the patient cradle as it extends through the bore 106. The device 132 is configured to dampen vibrations as the patient cradle 118 is extended through the bore 106. In embodiments, the vibrations are a result from the acceleration and deceleration of the patient cradle 118 through the bore 106. The device 132 may be configured to dampen vibrations resulting from moving the patient cradle 118 along the longitudinal axis 114, the vertical axis 124, or the lateral axis 126, or any combination thereof. By dampening the vibrations, high quality images can be obtained, as the patient remains in a same location without change due to vibrations during imaging and during movements.

Figure 2:
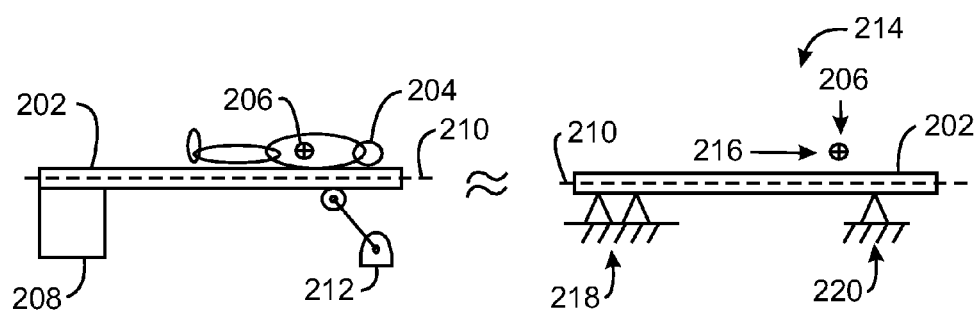
FIG. 2 is an illustration of a cantilevered patient support surface with a roller device.

FIG. 2 is an illustration of a cantilevered patient support surface 202. In embodiments, the patient support surface 202 is a patient table or a patient cradle that supports a patient 204 during an image data acquisition process. The patient 204 has a center of gravity at reference number 206. The patient support surface 202 may be supported at a first, left-most end by a pedestal 208. As the patient 204 is moved along a longitudinal axis 210 into an imaging bore, the patient support surface 202 may experience a deflection or sag at the end of the patient support surface 202 nearest the scanner bore. In the example of FIG. 2, the patient is moved from the left to the right to enter a scanner bore. The addition of a device 212 enables a constant deflection throughout an image data acquisition process at a single point of interest of the patient 204, thereby changing the patient support surface 202 from a cantilevered table, supported at one end, to a simply supported beam as illustrated by the free-body diagram 214 to dampen vibration.

Through the addition of the roller device 212 according to the present techniques, the advantages of a horizontally cantilevered surface for patient support while performing diagnostic imaging are maintained with the advantage of a simply supported system. For example, the constant sag or constant deflection enables a reduction in stair-step artifacts as discussed above. Additionally, the patient support surface can require vertical height adjustability to accommodate various patient sizes and to perform image optimization relative to the scanner bore. A cantilevered cradle system requires only one point of height adjustability, which is less complex when compared to a cradle system requiring two independent points of synchronized vertical adjustments. In embodiments, the simply supported system created by the addition of a roller device maintains a single point of height adjustability at the pedestal, while the roller device includes springs to maintain constant contact with the patient support system.

The free-body diagram 214 illustrates the patient center of gravity 206 as a shear force acting perpendicular to the longitudinal axis 210 of the patient support surface 202. An axial force 216 is a force from a cradle drive mechanism present that is used to move the cradle into the bore. The axial force 216 can also act to move the patient out of the bore. In embodiments, the axial force is supplied by a mechanical structure within the pedestal 208 that moves the patient support surface as necessary. A support 218 represents the beam support created by the pedestal 208. A support 220 represents the beam support created by the roller device 212. In embodiments, the support 220 is an upward force created by frictional resistance and an upwards spring bias of the roller device 212.

The height of the roller device 212 is adjustable due to springs of the device that compact and extend in order to maintain constant contact with the patient support surface 202. In this manner, deflection of the patient support surface is constant, eliminating vertical distance changes in the scanned image as a single point of interest passes through the FoV. Further, stair step artifacts that occur when successive axial scan images are stitched together are eliminated. The support surface with constant deflection according to the present techniques offers no or minimal change in vertical height for any part of the scanned anatomy during the entire scan acquisition process.

Figure 3:
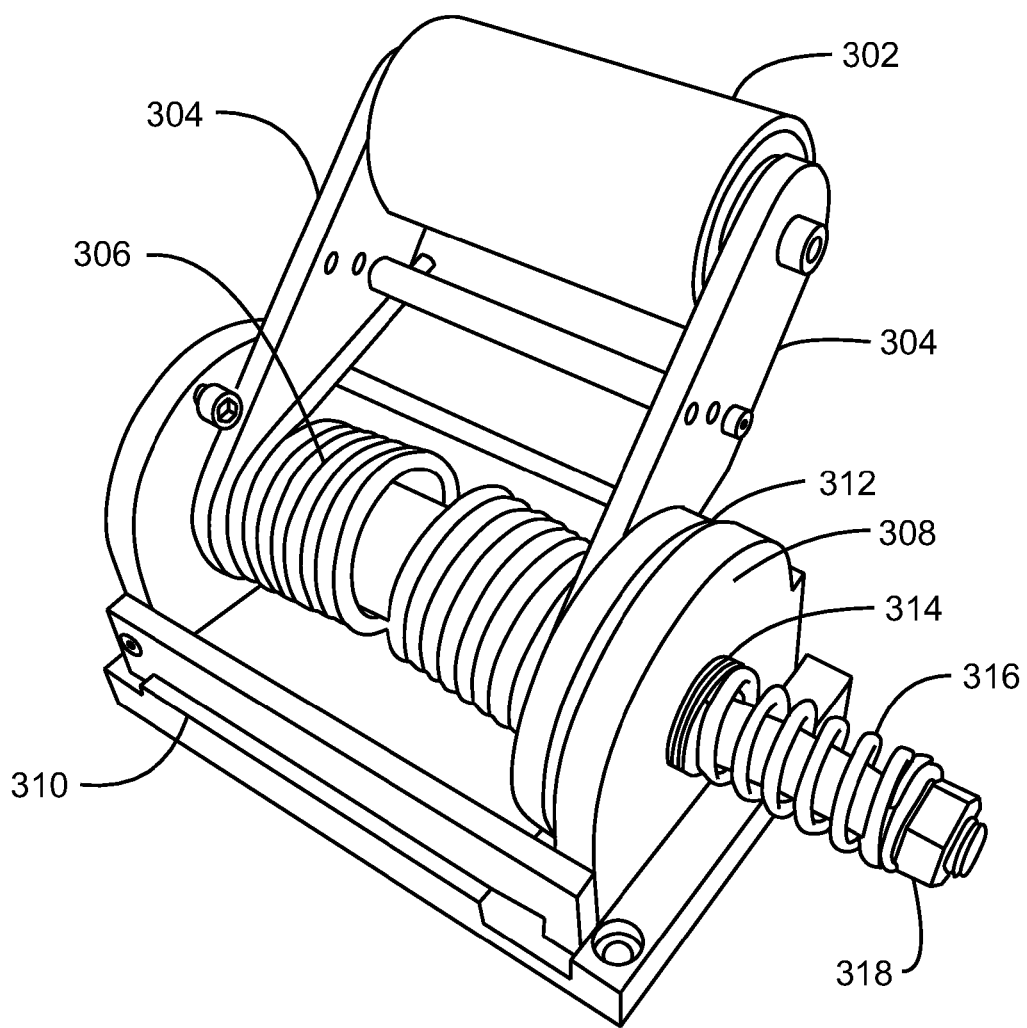
FIG. 3 is an illustration of a roller device.

FIG. 3 is an illustration of a roller device 300. The roller device 300 may be a device 132 (FIG. 1) or a roller device 212 (FIG. 2). The roller device 300 is configured to control vibrations created by a cantilevered cradle as the patient is moved into and out of the scanner bore. The cradle vibrates vertically as the patient's anatomy passes through the scanner FoV, creating undesirable scan image artifacts. As the cradle is extended, cradle tip vibrations increase. The roller device 300 is to reduce vibration in the image scan region and the cradle tip can be extended well beyond the scanner FoV with a constant deflection.

In embodiments, the roller device 300 controls small vibrations created when the patient is accelerated or decelerated during various scan motions with an upward force. In particular, the roller device creates a normal force acting upward on the cradle, which balances with the downward vibration force resulting in static equilibrium and preventing vibrations from occurring. The roller device 300 is located under the cradle and is continuously active during any and all cradle motions. The roller device 300 offers a small amount of vertical or upward force to support the cradle, yet enables the benefits of a cantilevered cradle system. The roller device 300 includes few moving parts and has adjustable features to custom tailor its performance.

The roller device 300 includes a roller 302. The roller 302 maintains constant contact with the cradle as discussed above. In embodiments, the roller 302 may be a urethane coated roller with ball bearings. The urethane coating on the roller may enable a hardness of approximately durometer 90A. Although a single roller is illustrated, the roller device may include a plurality of rollers that maintain constant contact with the cradle. The roller device may also include rollers of any shape, such as a spherical roller.

The roller 302 is coupled with a pair of roller lever arms 304. A plurality of torsion springs 306 are coupled with the roller lever arms 304 and are to enable constant roller contact with the cradle. The roller lever arms 304 and the torsion springs 306 are disposed within a side frame 308. The side frame is coupled with a base frame 310.

A friction disc 312 is disposed between the side frame 308 and a roller lever arm 304. Although a single friction disc 312 is illustrated to the right side of the roller device 300, a plurality of friction discs may be disposed on both sides of the roller device 300. The friction disc 312 rotates with the roller level arms 304 and contacts the side frame 308 during this rotation. In this manner, a friction resistance is created at the roller device 300. In embodiments, the friction disc 312 is stationary and the lever arm 304 rotates against the stationary friction disc. Thrust bearings 314 support an axial load from the die spring 316 as transmitted through side frame 308. An adjustable friction setting compression die spring 316 provides a normal force to pull the friction disc 312 against the side frame 308. In embodiments, the roller device 300 also includes internal radial bearings on a central shaft to support roller vertical forces, such as forces in a direction 124 (FIG. 1).

The roller device reduces the vertical vibrations or displacement by creating upwards pressure on the cradle which exceeds vibration forces created by cradle motions during imaging. Vertical forces acting on the device due to cradle vibration are very small, and typically less than ten pounds. The roller device 300 enables continuous upwards roller contact with the cradle bottom surface from the torsion springs 306. The frictional resistance created by the friction disc 312 is to counteract the small vibration forces. Cradle vibrations are quickly settled because the cantilevered support surface is now similar to a simply supported beam with two reactions supporting the cradle, rather than a single reaction of a pure cantilevered system. By setting the friction resistance higher than the vibration forces acting on the cradle, the roller 302 is held in position against the cradle when subjected to small vibration forces, therefore creating the simply supported beam.

The roller device 300 does not offer a significant amount of upward force, which could reduce the positive contributions of a pure cantilevered patient cradle. Additionally, the roller device 300 has features to adjust the amount of frictional resistance in response to the downward motion from the vibrations. For example, the adjustable friction setting compression die spring 316 can be adjusted to provide a higher or lower amount of normal forces to pull the friction disc 312 against the side frame 308 by turning a nut 318. Additionally, the upwards spring bias resulting from the torsion springs 306 can be changed by using different springs to change a spring rate of the springs. The spring mounting position may also be adjusted to change the upwards spring bias. In this manner, the device offers a balance between reducing and dampening vertical vibration motion while maintaining scanner imagining advantages of a cantilevered cradle. In embodiments, the torsion springs 306 can be replaced by extension or compression type springs in varying configurations with the device 300.

As discussed above, the roller device 300 uses torsion springs 306 to create an upwards force, enabling the roller to remain in constant contact with the cradle bottom surface. Torsion springs can accommodate all patient weights, but some changes in output force can occur during increased cradle deflection when heavy patient weight is applied. As described, the frictional resistance created by the friction disc 312 creates enough vertical support to overcome the downward directed vibration forces. The particular combination of both torsion spring and friction force may be used to ensure dampening of the vibration forces and a constant deflection at all positions of the cradle. In some embodiments, the upwards spring force is roughly three times greater than the friction force.

In embodiments, the friction disc 312 may have nearly identical static and dynamic friction coefficients. The friction disc is of a material that can dampen vibrations while also accommodating a wide range of cradle deflection due to varying patient weight. In other words, the friction material should have substantially equal static and dynamic coefficients of friction because the device accommodates a wide range of vertical motion. Additionally, roughly equal static and dynamic friction disc coefficients can be used to eliminating any stick-slip of the device. Stick-slip, as used herein, is a momentary positioning of the roller 302 without contact with the cradle. Thus, when stick-slip occurs the roller loses contact with the cradle for a brief period. Any disconnect in the roller system with the cradle will result in reduced effectiveness. In embodiments, the friction disc is constructed from Rulon-J, a plastic material often used in thrust bearing applications. The low break-away static and consistent dynamic friction characteristics of this material provide near constant friction force, thereby eliminating any stick-slip.

The block diagrams of FIGS. 1-3 are not intended to indicate that the roller device and system are to include all of the components shown in FIGS. 1-3 in every case. Moreover, any number of additional or alternative components not shown in FIGS. 1-3 may be included in the medical imaging system 100, depending on the details of the specific implementation.

Figure 4:
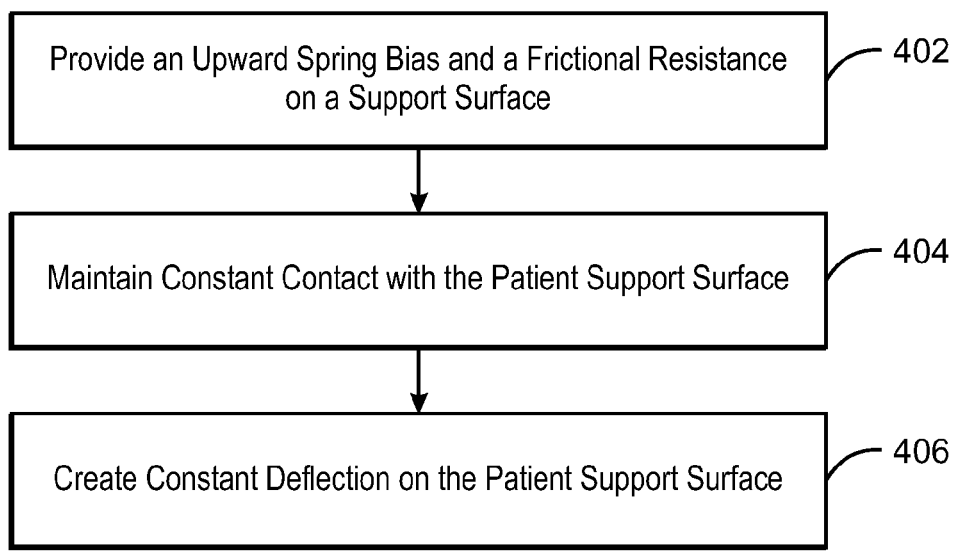
FIG. 4 is a process flow diagram of a method for converting a cantilevered support to act as a simply supported patient support for vibration control.

FIG. 4 is a process flow diagram of a method for converting a cantilevered support to act as a simply supported patient support for vibration control. At block 402, an upward spring bias and a frictional resistance is provided. As discussed above, the upward spring bias is a result of torsion springs of a roller device. The frictional resistance is provided by a friction disc. At block 404, constant contact is maintained with the patient support surface. In this manner, the upward spring bias and the frictional resistance have a constant contact with the patient support surface. In embodiments, identical static and dynamic friction disc coefficients are used to create constant contact with the patient support surface. At block 406, a constant deflection is created at the patient support surface, even during movements that occur during an image data acquisition process. The vibrations created when a patient is moved along the patient support surface are eliminated. As a result of the constant deflection, artifacts that may result when images are processed to create one image re reduced. In embodiments, the patient anatomy does not significantly change in vertical position throughout the entire image data acquisition.

Figure 5:
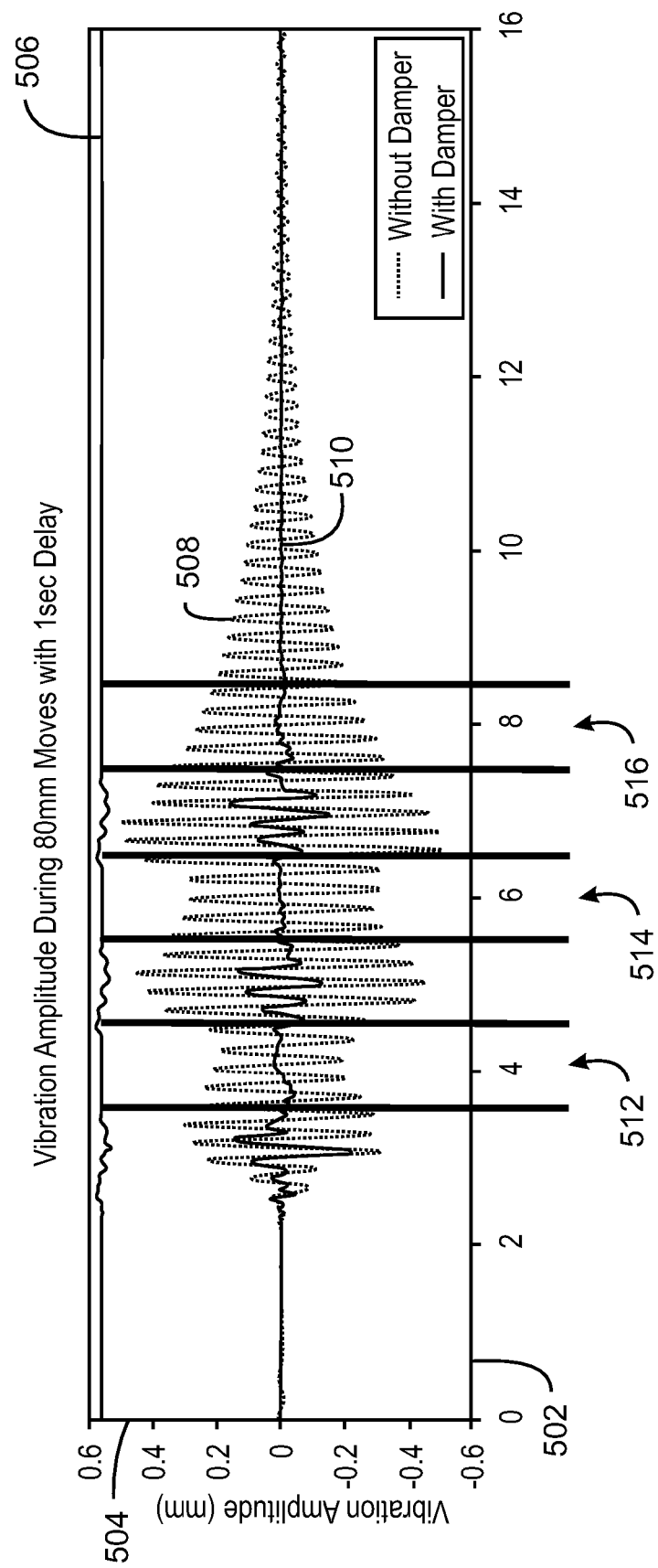
FIG. 5 is a chart illustrating vibrations from a patient support surface as described herein.

FIG. 5 is a chart illustrating vibrations from a patient support surface as described herein. The data was obtained during a simulated step and shoot image data acquisition process with an eighty millimeter travel distance, a one second delay between each move, and a five-hundred pound patient weight. The x-axis 502 of the chart represents time in seconds, while the y-axis 504 represents the amplitude of vibrations that occur in millimeters.

A line 506 represents a source of acceleration and deceleration movement of a patient support surface. A dotted line 508 represents a cantilevered patient surface without vibration control. A solid line 510 represents a patient surface with a vibration control damper, such as the roller device discussed above. The first scan occurs during a time period at reference number 512. Immediately prior to reference number 512, the patient support surface is moved into position, as illustrated by the line 506 immediately prior to approximately 3.5 seconds. During the first scan at reference number 512, the patient support surface without at damper at reference number 508 has a much larger vibration amplitude, when compared to the patient support surface with a damper at reference number 510. The vibration amplitude of the patient support surface without at damper at reference number 508 increases with each scan event at reference numbers 514 and 516 as the successive motion of the patient support surface continues to excite the system. The vibration amplitude of the patient support surface with a damper at reference number 510 stays relatively constant at each scan event 512, 514, and 515.

The cantilevered patient support surface with a damper, such as the device 132, 212, and 300 deflects and stays at constant deflection during an entire diagnostic imagining data acquisition process. This results in a significant reduction of scanner stair step artifacts because the cradle remains at constant deflection, other than small deflections which may occur due to the cradle support structure. The device described herein enables continuous self-adjustment and accommodates cantilevered cradle initial deflection due to various applied patient weight. In embodiments, the patient support surface could be curved or angled upwards or downwards. The device described herein can be used with patient support surfaces of various shapes and accommodates all changes in deflection angle for various parts of a cantilevered patient support. Additionally, the device is cost effective with relatively few moving parts with little or no service maintenance required.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A device comprising:
    a cantilevered cradle configured to support a patient;
    a base frame coupled with a plurality of torsion springs, the base frame attached to a friction setting compression die spring;
    a roller lever arm coupled with the plurality of torsion springs;
    a friction disc, wherein the plurality of torsion springs and the friction disc surround the roller lever arm, the friction disc urged against the base frame by the friction setting compression die spring; and
    a roller, wherein the roller lever arm is coupled to the roller, wherein the roller is urged against a free end of the cantilevered cradle by the plurality of torsion springs, wherein the friction disc provides a normal force against the free end of the cantilevered cradle to reduce vibration of the free end.

2. The device of claim 1, wherein the base frame comprises a stationary side frame, wherein the friction disc rotates with the roller lever arm and is urged against the stationary side frame by the friction setting compression die spring.

3. The device of claim 1, wherein the friction disc creates an upward force on the cantilevered cradle.

4. The device of claim 1, wherein the plurality of torsion springs creates an upward force on the cantilevered cradle.

5. The device of claim 1, wherein a frictional resistance from the friction disc and an upwards bias from the plurality of torsion springs is at a ratio of approximately 3:1.

6. The device of claim 1, wherein the friction setting compression die spring is adjustable.

7. The device of claim 1, wherein the roller comprises a urethane coated roller and ball bearings.

8. The device of claim 1, wherein the friction disc is stationary and the roller lever arm rotates against the friction disc.

9. The device of claim 1, wherein the friction disc has static and dynamic friction coefficients similar enough to avoid stick-slip of the device, wherein stick-slip is defined as a momentary positioning of the roller out of contact with the cantilevered cradle.

* * * * *